US007785289B2

(12) United States Patent
Rios et al.

(10) Patent No.: US 7,785,289 B2
(45) Date of Patent: Aug. 31, 2010

(54) CATHETER WITH FLEXIBLE, NON-KINKING ELONGATE MEMBER

(75) Inventors: Jaime Rios, San Diego, CA (US); Maritess E. Minas, San Diego, CA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 562 days.

(21) Appl. No.: 11/582,156

(22) Filed: Oct. 17, 2006

(65) Prior Publication Data

US 2008/0171976 A1 Jul. 17, 2008

(51) Int. Cl.
*A61M 29/00* (2006.01)
(52) U.S. Cl. .................................................. 604/96.01
(58) Field of Classification Search ............... 604/96.01
See application file for complete search history.

(56) References Cited

U.S. PATENT DOCUMENTS

| | | | |
|---|---|---|---|
| 5,931,812 | A | 8/1999 | Andersen et al. |
| 6,004,269 | A | 12/1999 | Crowley et al. |
| 6,352,534 | B1 | 3/2002 | Paddock et al. |
| 6,666,858 | B2 * | 12/2003 | Lafontaine .................. 606/21 |
| 7,011,655 | B2 | 3/2006 | Thompson et al. |
| 2003/0125709 | A1 * | 7/2003 | Eidenschink ............... 604/524 |
| 2004/0167466 | A1 | 8/2004 | Drasler et al. |
| 2004/0267338 | A1 * | 12/2004 | Harrison ..................... 607/105 |
| 2008/0077085 | A1 * | 3/2008 | Eidenschink et al. ..... 604/96.01 |

OTHER PUBLICATIONS

Avitall, et al., "New Cryotechnology for Electrical Isolation of the Pulmonary Veins," Journal of Cardiovascular Electrophysiology, vol. 14, No. 3, Mar. 2003, 6 pages.
Creganna—Intermediate Shaft Design, Creganna Medical Devices [online], Hypotube Shafts [retrieved Mar. 21, 2006] Retrieved from the Internet: URL: www.creganna.com/index.php?module=lhs &id=e369853df766fa44eledOff613f563bd > 2 pages.
Creganna—PTFE Coatings, Creganna Medical Devices [online] [retrieved Mar. 21, 2006] Retrieved from the Internet: URL: www. creganna.com/index.php?module=lhs&id= d645920e395fedad7bbbed0eca3fe2e0 >2 pages.
Creganna—Proximal Design, Creganna Medical Devices [online] [retrieved Mar. 21, 2006] Retrieved from the Internet: URL: www. creganna.com/index.php?module=lhs&id= 1c383cd30b7c298ab50293adfecb7b >2 pages.
Creganna—Hypotube Shaft, Creganna Medical Devices [online] [retrieved Mar. 21, 2006] Retrieved from the Internet: URL: www. creganna.com/index.php?module=lhs&id= 6364d3f0f495b6ab9dcf8d3b5c6e0b01 >2 pages.
Creganna Brochure "Pole Vault, the Gold Standard" retrieved Nov. 29, 2006, 2 pages.
Creganna Brochure "Distal Profile Design" retrieved Nov. 29, 2006, 1 page.

* cited by examiner

*Primary Examiner*—Nicholas D Lucchesi
*Assistant Examiner*—Jason Flick
(74) *Attorney, Agent, or Firm*—Fish & Richardson P.C.

(57) ABSTRACT

A catheter may include an elongate member and a distal end therapy-providing portion attached at a distal portion of the elongate member. The elongate member may have an outer generally tubular structure having, firstly, an inner tube structure of rigid material having a circumferential cut through at least a portion of a longitudinal length of the inner tube structure to allow bending of the circumferentially-cut portion of the inner tube structure while maintaining a substantially uniform cross-sectional area and shape at a point of bending, and secondly, a separate outer tube that surrounds and is spaced apart from at least the circumferentially-cut portion of the inner tube structure. The circumferential cut may be a helical cut having a pitch that may vary over the portion of the longitudinal length. An inner diameter of the outer tube may be approximately 0.003" greater than an outer diameter of the inner tube.

20 Claims, 7 Drawing Sheets

CATHETER WITH FLEXIBLE, NON-KINKING ELONGATE MEMBER

TECHNICAL FIELD

A catheter with a flexible, non-kinking elongate member is generally described.

BACKGROUND

A number of serious medical conditions may be treated in a minimally invasive manner with various kinds of catheters designed to reach treatment sites internal to a patient's body. One such medical condition is atrial fibrillation—a serious medical condition that results from abnormal electrical activity within the heart. This abnormal electrical activity may originate from various focal centers of the heart and generally decreases the efficiency with which the heart pumps blood. It is believed that some of these focal centers reside in the pulmonary veins of the left atrium. It is further believed that atrial fibrillation can be reduced or controlled by structurally altering or ablating the tissue at or near the focal centers of the abnormal electrical activity.

Cryotherapy, or the cooling of body tissue, is one method of ablating tissue of the heart and pulmonary veins to control atrial fibrillation. Cryotherapy may be delivered to appropriate treatment sites inside a patient's heart and circulatory system by a cryotherapy catheter. A cryotherapy catheter generally includes a treatment member at its distal end, such as an expandable balloon having a cooling chamber inside. A cryotherapy agent may be provided by a source external to the patient at the proximal end of the cryotherapy catheter and delivered distally through a lumen in an elongate member to the cooling chamber where it is released. Release of the cryotherapy agent into the chamber cools the chamber, and hence the balloon's outer surface that is put in contact with tissue to perform ablation. The cryotherapy agent may be exhausted proximally through an exhaust lumen in the elongate member to a reservoir external to the patient.

During a cooling cycle, there is generally a constant circulation of the cryotherapy agent to and from the distal part of the catheter, and it is important that the path of circulation not be disrupted. Any disruption in this path of circulation may present significant risks to the patient undergoing treatment. For example, disruptions in the circulation path may lead to loss of control of the cooling process, which may cause non-targeted tissue to be ablated. As another example, disruptions in the circulation path may lead to loss of control of pressure associated with a liquid-gas phase change in some cryotherapy agents inside the cooling chamber, which may result in uncontrolled expansion or rupture of portions of the catheter inside the patient.

The circulation path for the cryotherapy agent generally includes two separate lumens within an elongate member. One lumen fluidly couples the external cryotherapy source to the chamber of the balloon, and the other lumen is used for exhaust and fluidly couples the chamber of the balloon with the external reservoir. To maintain a circulation path, these lumens must be protected against being "pinched off," especially as the catheter is navigated through various turns—some of which may be sharp turns—in the vessels and organs of a patient's body.

SUMMARY

In some implementations, a catheter includes an elongate member and a distal end therapy-providing portion attached at a distal portion of the elongate member. The elongate member may have an outer generally tubular structure having, firstly, an inner tube structure of rigid material having a circumferential cut through at least a portion of a longitudinal length of the inner tube structure to allow bending of the circumferentially-cut portion of the inner tube structure while maintaining a substantially uniform cross-sectional area and shape at a point of bending, and secondly, a separate outer tube that surrounds and is spaced apart from at least the circumferentially-cut portion of the inner tube structure.

The therapy-providing portion may include a coolant chamber in which a cryo coolant is cycled, and the coolant chamber may be in fluid communication with at least one exhaust lumen that extends through the elongate member. The coolant chamber may include an expandable balloon. The therapy-providing portion may include an expandable balloon having one or more vacuum ports coupled to one or more vacuum lumens extending through the elongate member and adapted to remove material adjacent to the ports. The catheter may further include a guide lumen adapted to allow the catheter to traverse a prepositioned guidewire.

The circumferential cut may be a helical cut having a pitch characterized by a distance between two adjacent rotations of the helical cut. The pitch may vary over the portion of the longitudinal length. In particular, the pitch may be more fine near a distal end of the portion of the longitudinal length and more coarse near a proximal end of the portion of the longitudinal length. The circumferential cut may be discontinuous.

An inner diameter of the outer tube may be approximately 0.003" greater than an outer diameter of the inner tube. An outer diameter of the inner tube may be approximately 0.103" and an inner diameter of the outer tube is approximately 0.106."

In some implementations, a cryotherapy catheter includes a cryotherapy distal end portion having an inner chamber and an outer surface to contact body tissue to provide cryotherapy and an elongate member. The elongate member may have lumens formed therein that provide cryotherapy fluid from a proximal end of the elongate member to the distal end portion inner chamber and channel exhaust proximally from the distal end portion inner chamber. The elongate member may include an outer generally tubular structure having, firstly, an inner tube structure of rigid material having a circumferential cut through at least a portion of a longitudinal length of the inner tube structure to allow bending of the circumferentially-cut portion of the inner tube structure while substantially maintaining a uniform cross-sectional area and shape at a point of bending, and secondly, a separate outer tube that surrounds and is spaced apart from at least the circumferentially-cut portion of the inner tube structure.

The outer surface may include an expandable balloon. The expandable balloon may be adapted to contact substantially all of a circumference of an ostium of a patient's pulmonary vein when the expandable balloon is disposed inside the patient's left atrium and inflated substantially outside and adjacent to the pulmonary vein. The inner chamber may include a second expandable balloon. The expandable balloon may substantially surround the second expandable balloon to define a safety chamber that is in fluid communication with a vacuum lumen extending through the elongate member.

In some implementations, a method of manufacturing a cryotherapy catheter includes providing an elongate member having an outer structure forming an elongate flexible tube structure, and introducing within the flexible tube structure a rigid tube structure having a coiled cut therein through at least a portion of a longitudinal length of the rigid tube structure to allow bending of the rigid tube structure without pinching off an inner channel formed by the coiled-cut rigid tube structure.

The method may further include attaching a cryotherapy distal portion at a distal end of the elongate member. The method may further include extruding the elongate member apart from the rigid tube structure. Extruding the elongate member may include extruding the elongate member such that the elongate member has an inner diameter that is approximately 0.002" to 0.004" greater than an outer diameter of the rigid tube structure. The method may further include introducing within the rigid tube structure at least two lumens to supply the cryotherapy distal portion with cryo coolant and to exhaust the cryo coolant from the cryotherapy distal portion. The method may further include cutting the rigid tube structure in a coiled manner by rotating the rigid tube and longitudinally advancing the rigid tube relative to a cutting tool. Cutting the rigid tube structure may include cutting the rigid tube at a pitch that varies over a length of the portion of the longitudinal length.

The details of one or more implementations are set forth in the accompanying drawings and the description below. Other features, objects, and advantages will be apparent from the description and drawings, and from the claims.

BRIEF DESCRIPTION OF DRAWINGS

Like reference symbols in the various drawings indicate like elements.

DETAILED DESCRIPTION

Figure 1:
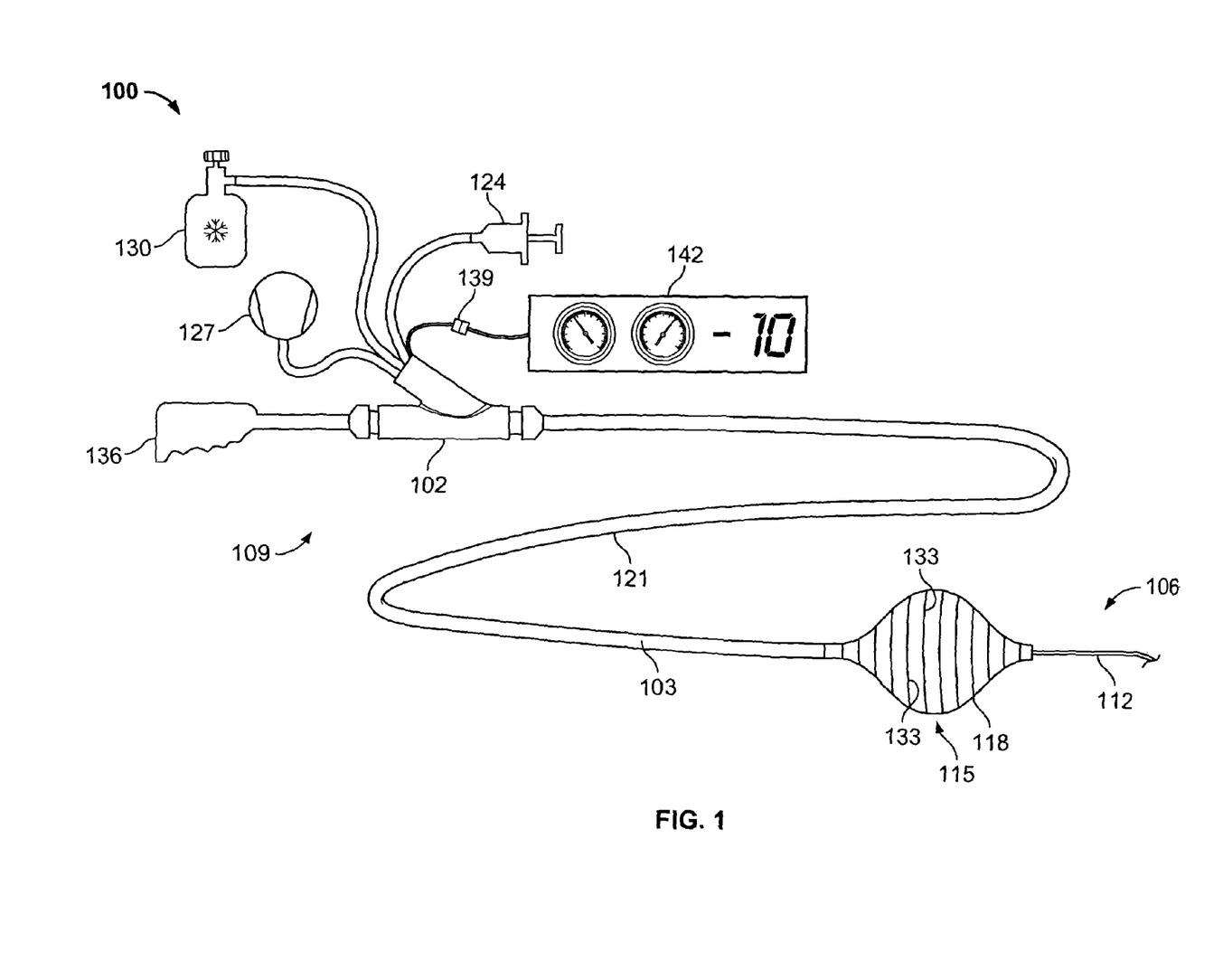
FIG. 1 is a side view of an example cryotherapy catheter.

An example cryotherapy catheter 100, shown in FIG. 1, includes an elongate member 121 that has an inflatable balloon 115 at a distal end 106. In some implementations, the balloon 115 has an internal chamber to which cryotherapy fluid is delivered to cool the internal chamber, the external surface 118 of the balloon 115, and adjacent body tissue. A port device 102 is attached to a proximal end 109 of the elongate member 121. The port device 102 provides connections to various external equipment, including a cryotherapy fluid source 130 and an exhaust reservoir 127.

The catheter's elongate member 121 has multiple internal lumens (not shown in FIG. 1). The lumens allow cryotherapy fluid to be delivered distally from the external cryotherapy fluid source 130 to the internal chamber of the balloon 115. In addition, the internal lumens of the elongate member 121 allow exhaust resulting from delivery of cryotherapy fluid to the internal chamber of the balloon 115 to be delivered proximally from the internal chamber 115 to the external exhaust reservoir 127. During operation, there may be continuous circulation within the elongate member 121 of cryotherapy fluid distally and exhaust proximally.

As will be shown in later figures, the catheter 100 may be used in procedures that require the elongate member 121 to be navigated through various turns of internal vessels and organs of a patient—some of which may be sharp turns. One such application is the use of the cryotherapy catheter 100 to treat atrial fibrillation by cooling or freezing various tissue in a patient's left atrium. The elongate member 121 has a structural design that allows it to accommodate sharp turns without the lumens of the elongate member 121 being "pinched off." In some implementations, as will be illustrated by way of example in later figures, this structural design includes a two-part outer flexible protective layer 103. One part of outer flexible protective layer 103 may include a circumferentially cut "hypotube," made of rigid material (e.g., stainless steel); the second part of the outer flexible protective layer 103 may include a flexible "skin" covering the circumferentially cut hypotube. With the outer flexible protective layer 103, the continuous flow of cryotherapy fluid and exhaust within the elongate member 121 is maintained, minimizing the possibility of the catheter rupturing within a patient's body because of the delivery or exhaust lumens being pinched off.

The example catheter 100 shown in FIG. 1 is an over-the-wire type catheter. Such a catheter uses a guidewire 112, which is shown in FIG. 1 extending from a distal end of the catheter. In some implementations, the guidewire 112 may be pre-positioned inside a patient's body; once the guidewire 112 is properly positioned, the balloon 115 (in a deflated state) and the elongate member 121 may be routed over the guidewire 112 to a treatment site. In some implementations, the guidewire 112 and balloon portion 115 of the catheter may be advanced together to a treatment site inside a patient's body, with the guidewire portion 112 leading the balloon 115 by some distance (e.g., several inches). When the guidewire portion 112 reaches the treatment site, the balloon may then be advanced over the guidewire 112 until it also reaches the treatment site.

The catheter 100 includes a manipulator 136, by which a medical practitioner may navigate the guidewire 112 and balloon 115 through a patient's body to a treatment site. In some implementations, release of cryotherapy fluid into the cooling chamber may inflate the balloon 115 to a shape similar to that shown in FIG. 1. In other implementations, a pressure source 124 may be used to inflate the balloon 115 independently of the release of cryotherapy fluid into the internal chamber of the balloon 115. The pressure source 124 may also be used to inflate an anchor member on the end of the guidewire 112 (not shown). The catheter 100 includes a connector 139 for connecting monitoring equipment 142. The monitoring equipment may be used, for example, to monitor temperature or pressure at the distal end of the catheter. To aid in positioning the treatment member 115 of the catheter 100 inside a patient's body, various marker bands 133 are also disposed at the distal end 106 of the catheter 100. The marker bands 133 may be opaque when the catheter is viewed by x-ray or other imaging techniques.

In some implementations, the balloon 115, and a corresponding internal cooling chamber, if present (e.g., balloon 321, shown in FIG. 3A), may be formed from a polymer including, but not limited to, polyolefin copolymer, polyester, polyethylene teraphthalate, polyethylene, polyether-blockamide, polyamide, polyimide, nylon, latex, or urethane. For example, certain implementations of the balloon 115 comprise PEBAX® 7033 material (70D poly ether amide block). The balloon 115 may be made by blow-molding a polymer extrusion into the desired shape. In some embodiments, the balloon 115 may be constructed to expand to a desired shape when pressurized without elastically deforming substantially beyond the desired shape.

A number of ancillary processes may be used to affect the material properties of the balloon 115. For example, the polymer extrusion may be exposed to gamma radiation which alters the polymer infrastructure to provide uniform expansion during blow molding and additional burst strength when in use. In addition, the molded balloon 115 may be exposed to a low temperature plasma field which alters the surface properties to provide enhanced adhesion characteristics. Those skilled in the art will recognize that other materials and manufacturing processes may be used to provide balloon 115 (and any internal balloon(s)) suitable for use with the catheter.

Figure 2:
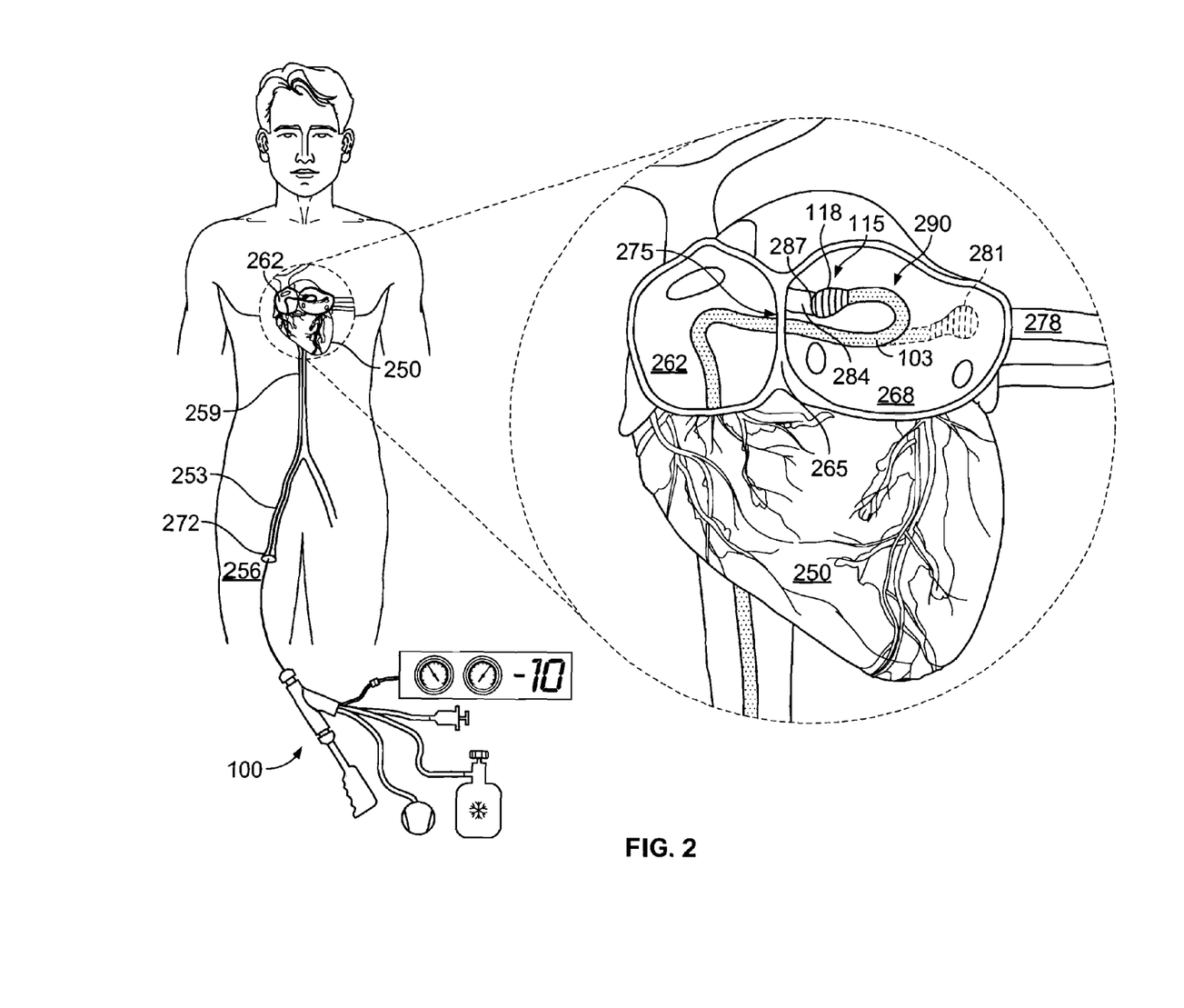
FIG. 2 illustrates an example application to a patient in which the catheter of FIG. 1 may used.

FIG. 2 illustrates an example application in which the catheter 100 of FIG. 1 may be navigated through sharp turns of a patient's body. In this example, the catheter 100 may deliver cryotherapy to the left atrium 268 of a patient's heart 250 in order to treat atrial fibrillation.

To get the catheter 100 to the patient's left atrium 268, a medical practitioner may obtain access to the patient's circulatory system at the patient's femoral vein 253. In particular, the medical practitioner may insert a sleeve or sheath 272 into the patient's femoral vein 253 to keep an access point open during the procedure. The medical practitioner may then advance the guidewire through the sheath 272, into the femoral vein 253 in the patient's upper leg 256, into the inferior vena cava 259, and into the patient's right atrium 262. The medical practitioner may then puncture the septum 265. In particular, the medical practitioner may route a transseptal needle (not shown) over the guidewire, puncture the septum with the transseptal needle to create an access point 275, withdraw the transseptal needle, then advance the guidewire through the access point 275 into the patient's left atrium 268. Once the guidewire is in the patient's left atrium 268, the medical practitioner may advance it further into one of the patient's pulmonary veins and anchor it there. For example, the medical practitioner may initially anchor the guidewire inside the right superior pulmonary vein 284.

Next the medical practitioner may advance the cryo balloon 115 portion of the catheter 100 over the guidewire to just outside the ostium 287 of the pulmonary vein 284 in which the guidewire is anchored. In some implementations, the medical practitioner may then inflate the cryo balloon 115 such that its exterior surface 118 contacts tissue at the circumference of the ostium 287; then the medical practitioner may initiate one or more cooling cycles to ablate the tissue of the ostium 287. In some implementations, the medical practitioner may initiate one or more cooling cycles without first inflating the cryo balloon 115. In the latter implementations, release of cryotherapy fluid into the cryo balloon 115 may itself inflate the cryo balloon 115, causing its outer surface 118 to contact and ablate the tissue of the ostium 287.

In some implementations, position of the cryo balloon 115 may be adjusted between cooling cycles. For example, the inflated cryo balloon 115 may be smaller than the ostium being treated; accordingly, each cooling cycle may only ablate tissue along a portion of the circumference of the ostium 287. To treat tissue all the way around, the cryo balloon 115 may be repositioned, and additional cooling cycles may be performed. In some implementations, as shown, the cryo balloon 115 is sized such that, when inflated and appropriately positioned, it contacts tissue substantially all the way around the circumference of an ostium 287, so that no repositioning is required during treatment of a single ostium.

In some implementations, the cryo balloon 115 is steerable independently of any guidewire. That is, even though a guidewire may generally guide the path of the cryo balloon 115 and other portions of the treatment member, the position of the cryo balloon 115 may be fine-tuned with an independent steering system. Various methods of steering catheters and guidewires are known and are not described in detail here.

Once the tissue of one ostium 287 has been treated, the catheter 100 may be repositioned to treat other ostia. To reposition the catheter 100, the cryo balloon 115 may be deflated and the catheter 100 withdrawn enough to permit the guidewire to be repositioned in another ostium. Repositioning the guidewire may involve deflating an anchoring member associated with the guidewire (not shown), withdrawing the guidewire from the first pulmonary vein 284, steering it to another pulmonary vein (e.g., the left superior pulmonary vein 278), and re-anchoring it in the new pulmonary vein. The catheter 100 may then be positioned just outside the ostium 281 of the new pulmonary vein 278 and the cryo balloon 115 may be inflated, such that its outer surface 118 contacts tissue along the circumference of the ostium 281. After the cryo balloon 115 is appropriately positioned, one or more cooling cycles may be initiated to ablate the tissue of this ostium.

This process may be repeated for the other ostia, such that annular conduction blocks are created in multiple ostia. Once the entire therapy process has been completed, the cryo balloon 115 may again be deflated, and the treatment member 115 may be removed from the patient. Similarly, the guidewire may be removed.

Although the example procedure described above is in the context of a catheter having a guidewire, the procedure of ablating tissue with a cryo balloon catheter may also be performed with a fully steerable catheter that lacks a corresponding guidewire. Fully steerable catheters that do not have corresponding guidewires are known in the art and are not described here in detail, as the exact structure of the steering mechanism of the catheter is not critical to this document; any appropriate steering mechanism may be used to advance the catheter to various treatment sites.

Because of their position relative to the septum access point 275, certain pulmonary ostia may be easier to reach than others. For example, referring to FIG. 2, the left superior pulmonary ostium 281 is relatively in-line with the septum access point 275. In contrast, the ostium 287 of the right superior pulmonary vein 284 is less directly accessible from the septum 265 access point 275 and may require the catheter to be navigated through a relatively sharp bend 290. Without the two-part outer flexible protective layer 103 that is described in greater detail with reference to the remaining figures, the lumens inside the catheter 100 may be prone to constriction as the catheter 100 is navigated through sharp bends, such as the bend 290 required to reach the right superior pulmonary ostium 287. For example, a catheter with too flexible of an outer layer may develop a kink that constricts the internal lumens (e.g., the cryotherapy exhaust lumen). The possibility of constricting internal lumens may give rise to significant risks to the patient, as it may lead to loss of precise control of the balloon 115 or of the cryotherapy process, or limit the ability to exhaust the cryotherapy agent from the balloon 115. Inclusion of the two-part flexible protective outer layer 103, which is less prone to constriction when the catheter is navigated through sharp bends, may reduce these risks.

Figure 3A:
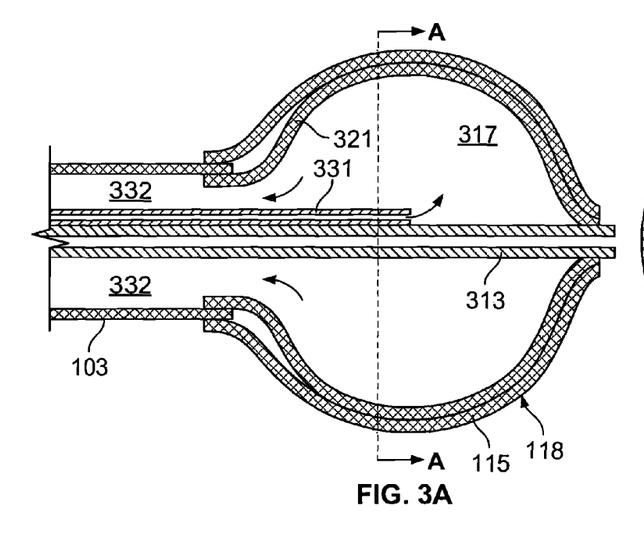
FIG. 3A is a longitudinal cross-sectional view of the balloon portion of the catheter that is shown in FIG. 1.
Figure 3B:
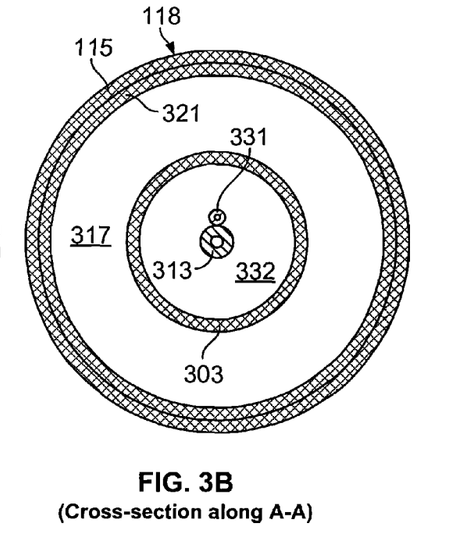
FIG. 3B is a cross-sectional view of the balloon portion of the catheter that is shown in FIG. 3A.

FIG. 3A shows a longitudinal cross-section of the example cryotherapy balloon 315 and the example two-part flexible protective layer 103, that maintains the paths by which cryotherapy fluid and exhaust may be cycled to an from an internal chamber of the cryotherapy balloon 115. FIG. 3B shows a radial cross-section along the line A-A that is shown in FIG. 3A. As shown in FIG. 3A, cryotherapy coolant may be delivered from an external source (e.g., 130 in FIG. 1) to a cooling chamber 317 internal to the balloon 315, via a cryotherapy coolant delivery lumen 331. The coolant may be released into the cooling chamber 317 from an opening at the end of the delivery lumen 331, or the coolant may be released through a cryotherapy device 319 (see FIG. 3C) disposed at the end of the delivery lumen 331. In some implementations, the coolant undergoes a phase change within the cooling chamber, cooling the chamber 317 via the so-called Joule-Thomson effect, as well as cooling the external surface 118 of the outermost balloon 115 and a patient's body tissue that is adjacent to the external surface 318 of the outer balloon. The cryotherapy fluid, or gas if the fluid has undergone a phase change, is then exhausted through an exhaust lumen 332 to a reservoir (e.g., 127 in FIG. 1) or vacuum source external to the catheter.

In some implementations, there is a continuous cycle of cryotherapy fluid to the cooling chamber 317 via the delivery lumen 331 and exhaust from the cooling chamber 317 via the exhaust lumen 332. For proper operation of the cryotherapy catheter, this continuous cycle must be carefully maintained; that is, the delivery lumen 331 and the exhaust lumen 332 must both be protected against being pinched off, even if the catheter is subjected to sharp turns inside a patient.

Figure 3C:
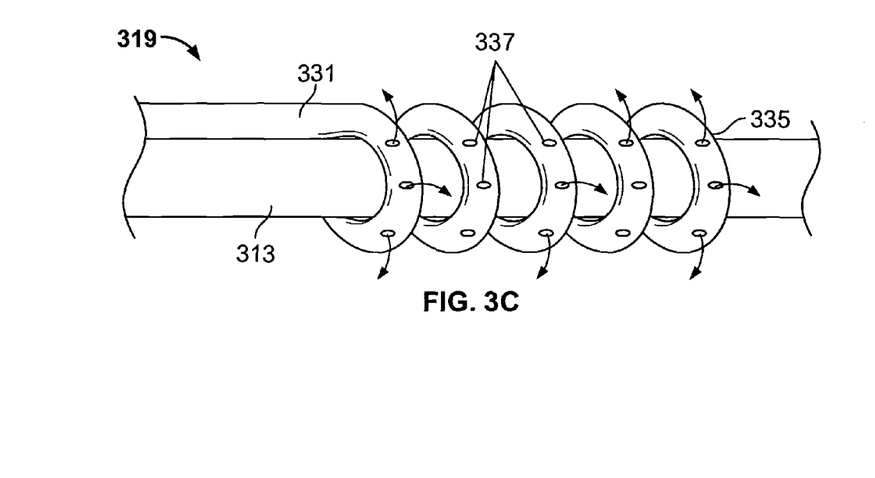
FIG. 3C is a perspective view of an example cooling member that may be disposed within the cryotherapy balloon.

In over the-wire implementations, the cryotherapy catheter includes a guidewire lumen 313, which allows the balloon 115 to be routed to a treatment site inside a patient over a pre-positioned guidewire (not shown in FIG. 3A, 3B or 3C). In some implementations, the cooling device 319 includes a coiled extension 335 having a number of apertures 337 from which pressurized liquid coolant can escape and change state to a gas (see FIG. 3C). In some implementations, the exhaust lumen 332 may be defined generally by the flexible protective layer 103 itself, as shown. In some implementations, the catheter may include one or more dedicated exhaust lumen structures (not shown) that are defined independently of the flexible protective layer 103.

The coolant that is cycled into the balloon 115 is one that will provide the appropriate heat transfer characteristics consistent with the goals of treatment. In some implementations, liquid $N_2O$ may be used as a cryo coolant. When liquid $N_2O$ is used, it may be transported to the cooling chamber 317 in the liquid phase where it evaporates from the end of the coolant delivery lumen 331, or from the apertures 337 of a cooling device 319. Other implementations may use Freon, Argon gas, and $CO_2$ gas as coolants. Further, some implementations may use coolants that enter and exit the cooling chamber 317 as a liquid, such as Fluisol, or a mixture of saline solution and ethanol.

In some implementations, as shown, a second balloon 321 may be provided within the outer balloon 115 to isolate the cryotherapy coolant within the cooling chamber 317. In these implementations, the outer balloon 115 forms a safety chamber that prevents coolant from escaping if the cooling chamber 317 balloon 321 bursts. A separate vacuum lumen (not shown) may be provided to evacuate any gas or liquid that escapes from the internal cooling chamber 317. In operation, the outer and inner balloons 115 and 321 may expand and deflate together. In some implementations, release of coolant inflates the balloons 115 and 321. In some implementations, the balloons 115 or 321 are first inflated by the injection of an inflation fluid or gas (e.g., a saline solution or an inert gas), after which the coolant may be introduced to the cooling chamber 317.

As shown in FIG. 3B, the coolant delivery lumen 331 is adjacent to the guidewire lumen 313, and the guidewire lumen is shown to be substantially coaxial with the exhaust lumen 332, which corresponds to the overall shaft of the catheter. In some implementations, lumens may have other arrangements, and more or fewer lumens may be included in the catheter. For example, the coolant delivery lumen 331 may be disposed coaxially around the guidewire lumen 331; the guidewire lumen 331 may be omitted in a steerable catheter design; lumens for steering members may be provided; one or more vacuum lumens may be included; one or more exhaust lumens may be included that are independent of the outer layer 303 of the catheter shaft; additional lumens may be provided for inflating or deflating the balloons 315 or 321 or for inflating or deflating other balloons not shown in FIG. 3A; and additional lumens may be provided to control an anchor member that may be disposed on a guidewire near the distal portion of the balloon 315. Various other modifications may be made to the catheter without departing from the spirit of this document.

Figure 4A:
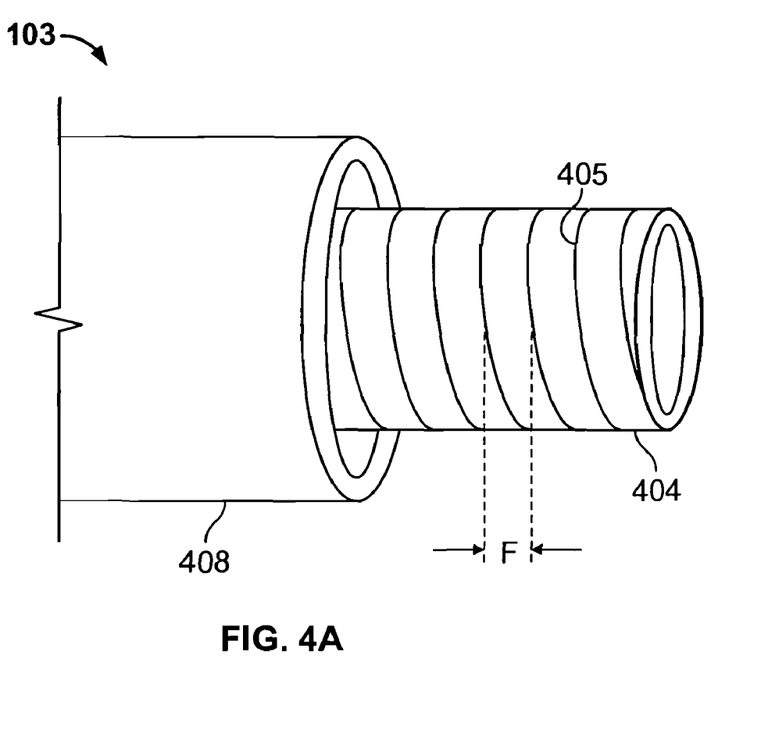
FIG. 4A shows additional details of the elongate member portion of the catheter that is shown in FIG. 1.
Figure 4B:
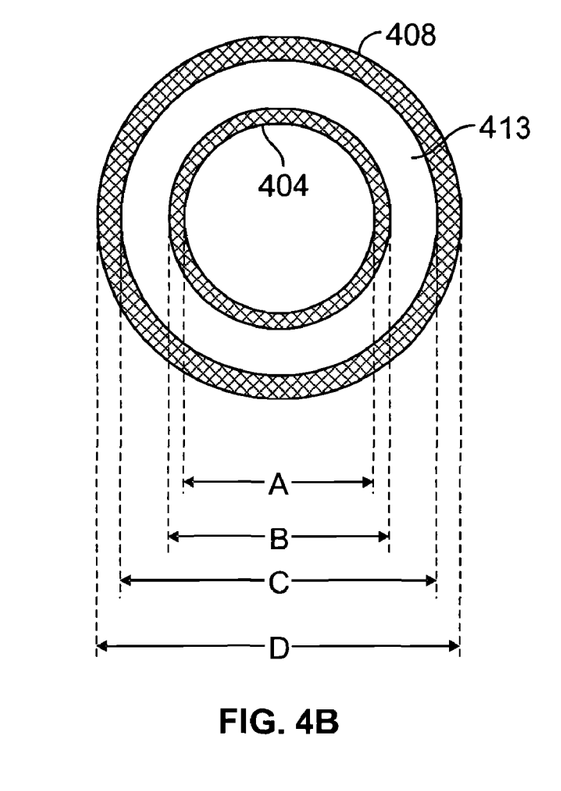
FIG. 4B is a cross-sectional view of the elongate member portion that is shown in FIG. 4A.
Figure 4C:
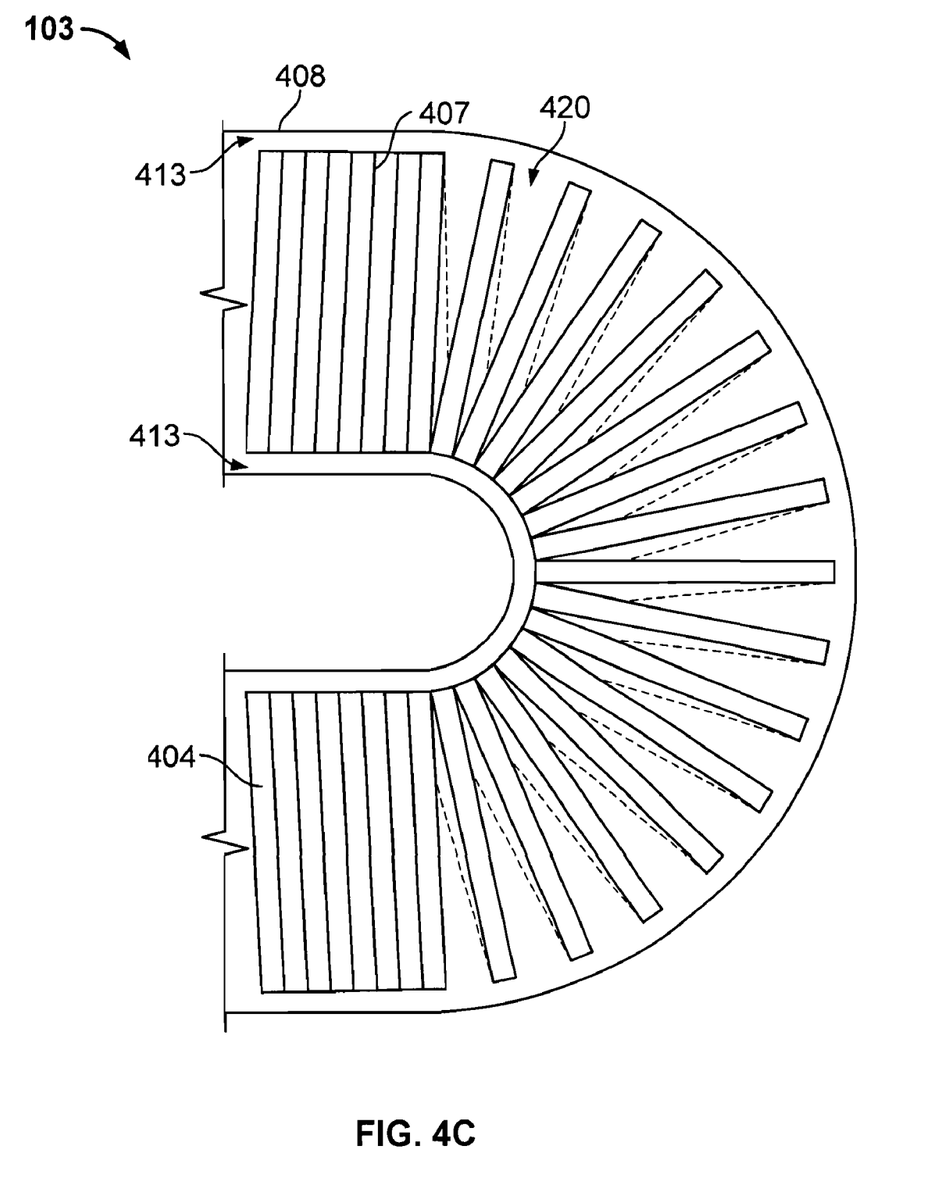
FIG. 4C is a longitudinal cross-section of the elongate member portion that is shown in FIG. 4A, as that portion is subjected to a sharp turn.

FIGS. 4A, 4B and 4C illustrate additional details of an example two-part flexible protective layer 103 that prevents lumens internal to the elongate member of a catheter from being pinched off. Some implementations of the flexible protective layer 103 include a hypotube 404—a rigid material (e.g., stainless steel) that may protect the shaft of the catheter (e.g., elongate member 121 in FIG. 1) from kinking and from radial forces that might otherwise constrict lumens internal to the hypotube 404. To provide flexibility, the hypotube 404 may be circumferentially cut or grooved. For example, as shown, the hypotube 404 includes a generally helical cut 405 that extends all the way through the thickness of the tube. The helical cut may have a fixed controlled pitch 407, or the pitch of the cut may vary. As shown in FIG. 4A, the cut has a fixed pitch "F" (e.g., 0.025"). In some implementations, the rigidity of the hypotube material and the flexibility provided by the circumferential cut 405 in the hypotube material combines to provide a protective layer 403 for the catheter that optimizes flexibility, pushability, trackability and transmission of torque along the length of the catheter.

As described above, the flexible protective layer 103 may form the outer layer of a catheter shaft (e.g., the elongate member 121 shown in FIG. 1). In some implementations, the flexible protective layer 103 may also comprise a lumen that is disposed internal to the outer wall of a catheter shaft. More particularly, in some implementations, the flexible protective layer 103 comprises an internal exhaust lumen for exhausting cryotherapy coolant from a cryo balloon. In these implementations, the flexible protective layer may generally be used to protect specific lumens from being constricted when the catheter is subjected to sharp, small-radius bends.

To somewhat stiffen an otherwise very flexible, circumferentially cut hypotube 404, an additional layer 408 of flexible material may be disposed outside the hypotube 404. This additional outer layer 408 may also provide an impermeable barrier that prevents, for example, cryotherapy coolant from leaking out of the catheter. In some implementations, the outer layer 408 may include a polymer such as, PEBAX™. In some implementations, the outer layer 408 may be sized to have an inside diameter "C" that is greater than the outside diameter "B" of the hypotube 404, such that a radial gap 413 exists between the outer layer 408 and the hypotube 404. For example, in some implementations, as shown (not to scale), the hypotube 404 has an inside diameter "A" of 0.095" and an outside diameter "B" of 0.103"; the outer layer 408 may have an inside diameter "C" of between 0.105" and 0.107" and an outside diameter "D" of approximately 0.131" or less. The size of the gap may affect the flexibility of the overall structure 103. For example, a catheter with a larger gap 413 may be more flexible than a catheter with a smaller gap 413 between the outer layer 408 and the hypotube 404. As is described in further detail with reference to FIG. 6, the hypotube 404 and outer layer 408 may be manufactured separately and subsequently combined in order to precisely determine the gap 413. For example, rather than extruding the outer layer 408 over the top of the circumferentially cut (405) hypotube 404, the outer layer 408 may be independently extruded and subsequently installed over the hypotube 404.

FIG. 4C provides a cross-sectional view (not to scale) of an example flexible protective layer 103 of an elongate portion of a catheter as that elongate portion is subjected to a sharp turn or bend. As described with reference to FIGS. 4A and 4B, the flexible protective layer includes an inner hypotube member 404 having a circumferential cut 407, and flexible outer layer 408 spaced apart radially from the hypotube member 404 by a small gap 413. As shown in FIG. 4C, when the flexible protective layer 103 is straight, the "ribbons" of the hypotube 404 formed by the circumferential cuts 407 remain tight against adjacent ribbons. As the flexible protective layer is bent, the ribbons separate at their outer edge, leaving an axial gap 420. In spite of the axial gap, the rigidity of each individual ribbon exerts an outward radial force that prevents lumens internal to the flexible protective layer 403 from being pinched off.

In some implementations, a variation in flexibility across the length of the catheter may be desirable. For example, referring to FIG. 1, the distal end 106 of the shaft 121, near the cryo balloon 115, may require sufficient flexibility to be routed to, for example, a patient's right superior pulmonary vein. As shown in FIG. 2, routing the treatment member 215 from the access point 275 in the septum 265 to the right superior pulmonary vein 284 may force the catheter 100 through a sharp bend 290, having a very small radius. Accordingly, this portion of the catheter 100 may require substantial flexibility. Other portions of the catheter 100 may require less flexibility. For example, referring again to FIG. 2, the other bends required to route a catheter 100 from the upper leg 256 of a patient to the patient's right atrium 262 may have much larger radii and may accordingly require less flexibility. To route the catheter 100 through these more gradual bends, characteristics such as pushability, trackability and torque transmission may be more important than extreme flexibility.

Figure 5A:
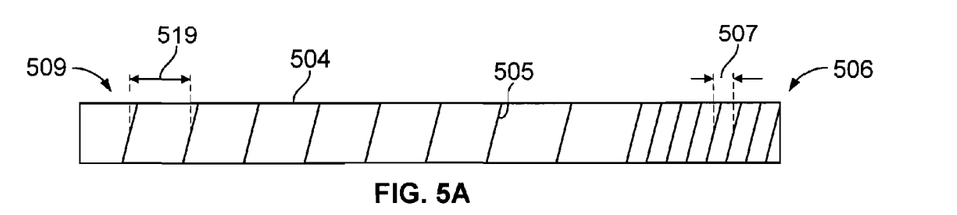
FIGS. 5A-5D illustrate various circumferential cuts in a portion of an example flexible protective layer of the elongate portion of a catheter.
Figure 5B:
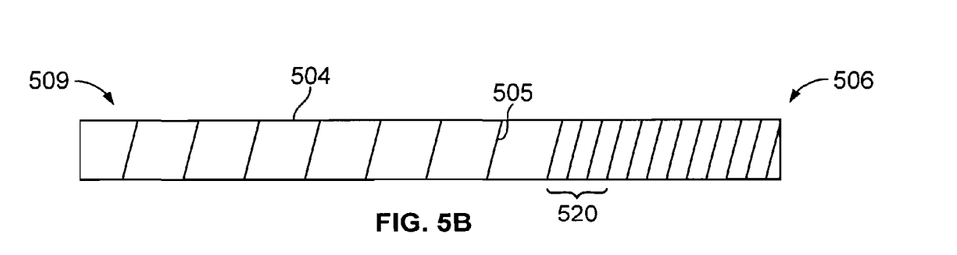
Figure 5C:
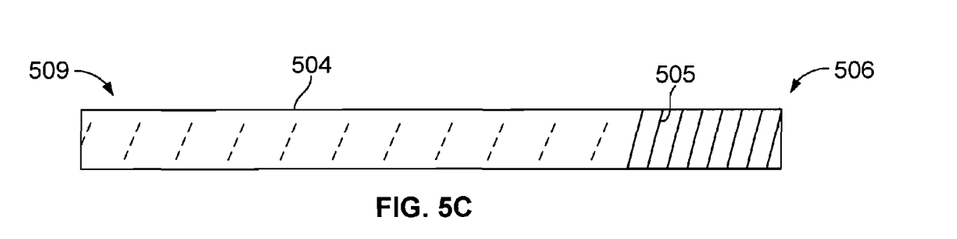
Figure 5D:
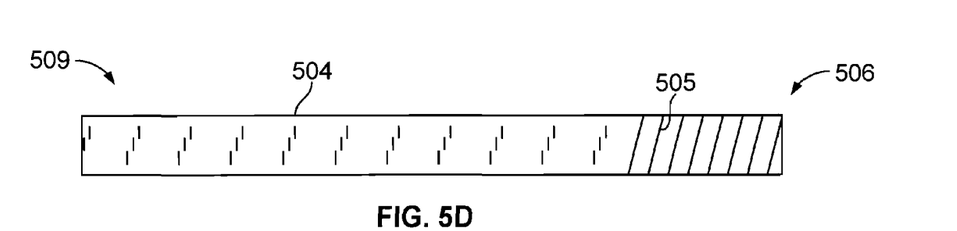

To vary the flexibility and increase the pushability, trackability and torque transmission characteristics, the pattern of circumferential cuts may be varied over the length of the hypotube. Several example variations in circumferential cuts are illustrated in FIGS. 5A-5D. For example, referring to FIG. 5A, the pitch 507 of the circumferential cuts 505 near the distal end 506 of a hypotube 504 may be much finer than the pitch 519 near the proximal end 509 of the hypotube 504. In some implementations, the pitch may vary gradually over the length of the hypotube, as shown in FIG. 5A. In some implementations, the pitch may change relatively rapidly within a small portion 520 of the hypotube, as shown in FIG. 5B. In some implementations, the circumferential cut 505 may be discontinuous along one or more portions of the length of the hypotube 504, as shown in FIG. 5C.

The cuts may have various angles relative to the length of the hypotube, depending upon the process by which the cuts are made. For example, in some implementations, the hypotube 504 may be turned and longitudinally advanced relative to a cutting tool, such as a diamond saw or cutting laser, resulting in a substantially helical cut whose pitch varies based upon the speed at which the tube is turned and longitudinally advanced. In some implementations, the hypotube 504 may simply be rotated relative to a cutting tool without being longitudinally advanced, resulting in cuts that are substantially perpendicular to the length of the hypotube (see FIG. 5D).

Figure 6:
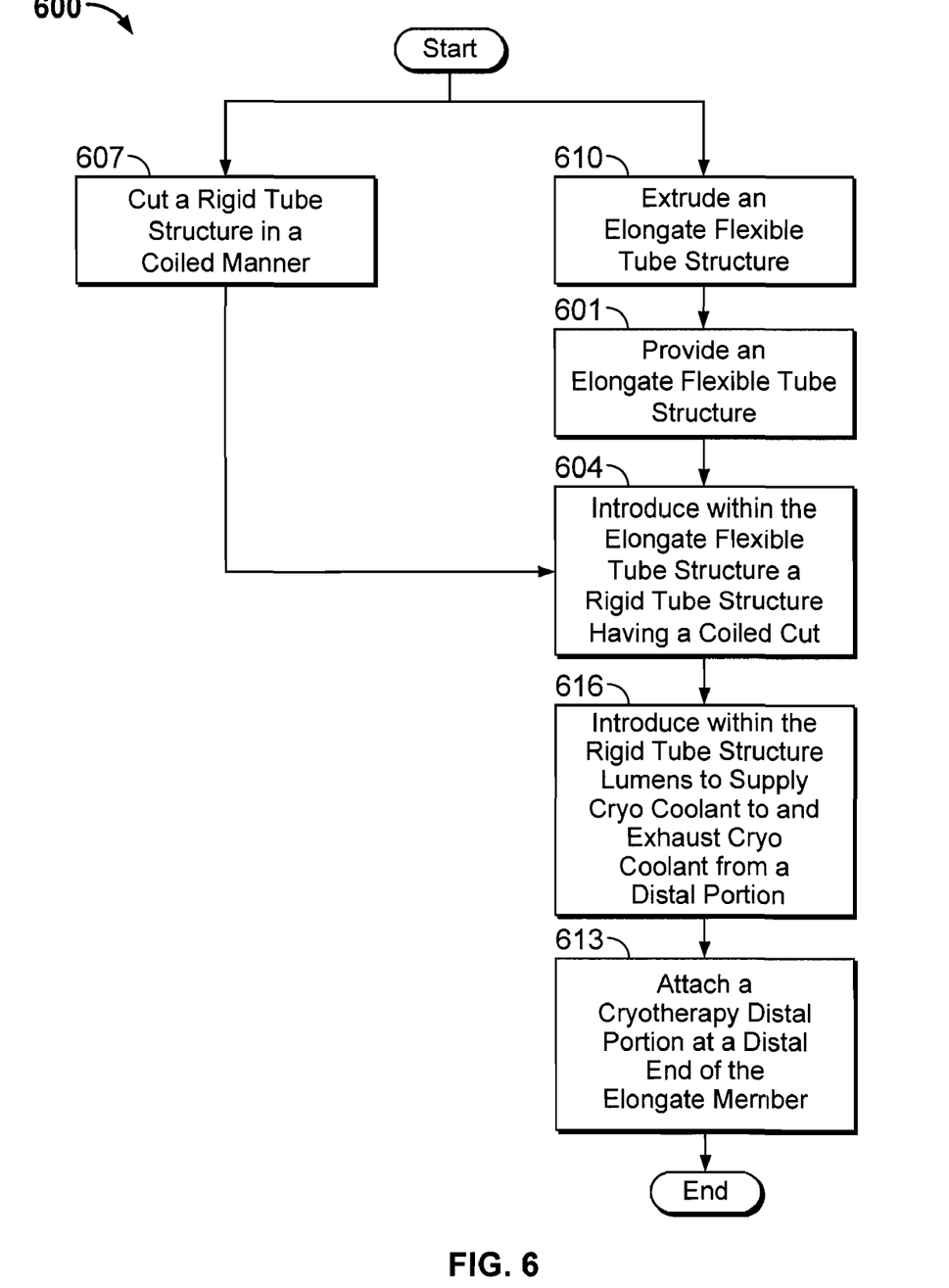
FIG. 6 is a flow diagram of one method of manufacturing a flexible protective layer for a catheter shown in the previous figures.

FIG. 6 is a flow diagram of one example method 600 of manufacturing the two-part flexible protective layer of a cryotherapy catheter shown in the previous figures. The method 600 includes providing (601) an elongate flexible tube structure. The elongate flexible tube structure may be an extruded flexible tube made from a material such as PEBAX™ or other material that is suitable for contact with internal body cavities and vessels. The method 600 further includes introducing (604) within the elongate flexible tube a rigid tube structure having a coiled cut. In some implementations, the rigid tube structure is a stainless steel hypotube having a helical laser cut with a pitch characterizing a distance between two adjacent rotations of the helical cut. The pitch may vary over the length of the hypotube and may be designed to provide varying amounts of flexibility over the length of the hypotube. Flexibility may be balanced with other characteristics such as pushability or transmission of torque along portions of the hypotube. For example, the hypotube may have a very fine pitch near what will become the distal end of the corresponding cryotherapy catheter, to provide greater flexibility, and a more coarse pitch near what will become the proximal end of the corresponding cryotherapy catheter, to provide greater pushability, trackability and transmission of torque.

Prior to being introduced into the elongate flexible tube, an uncut hypotube may be cut (607) in a coiled manner. For example, the hypotube may be rotated and longitudinally advanced relative to a cutting tool such as an appropriately sized diamond saw or a cutting laser. The pitch of the cut may vary based on the speed at which the hypotube is longitudinally advanced. In some implementations, the hypotube may be rotated but not advanced, resulting in various discontinuous cut patterns. In some implementations, the hypotube may be rotated and longitudinally advanced, but the cut may be discontinuous, resulting in various other discontinuous cut patterns. Some of the many possible cut patterns are described above with reference to FIGS. 5A-5D.

The elongate flexible tube structure may be extruded (610) apart from the cut hypotube. By extruding (610) the flexible tube structure apart from the hypotube, the flexible tube structure may be formed to have an inside diameter that is sufficiently greater than the outside diameter of the hypotube such that the flexibility of the hypotube is maintained. In some implementations, the difference between the inner diameter of the flexible tube structure and the outer diameter of the hypotube is between about 0.002" and about 0.004". For example, in some implementations, the hypotube has an outside diameter of 0.103" (and, for example, an inside diameter of 0.095") and the inside diameter of the flexible tube structure ranges between 0.105" and 0.107" (with an outside diameter of less than or equal to about 0.131"—a "10 French" size catheter).

A cryotherapy distal portion may be attached (613) to a distal end of the elongate member. The cryotherapy distal portion may comprise one or more expandable balloons adapted to transfer heat from tissue adjacent to the surface of the outer expandable balloon to a cryo coolant inside the balloon.

Before or after the cryotherapy distal portion is attached (613) to the distal end of the elongate member, lumens may be introduced (616) within the rigid tube structure. At least one lumen may be provided to supply coolant to the cryotherapy distal portion, and at least one lumen may be provided to exhaust coolant from the cryotherapy distal portion. In some implementations, as described above, cryo coolant is transported in the coolant supply lumen to the expandable balloon as a liquid and exhausted from the balloon as a gas. Other lumens may also be introduced (616). For example, a central guidewire lumen may be provided, and other lumens may be provided for a catheter steering mechanism, for inflating or deflating the balloon, or for removing material adjacent to the balloon.

The method 600 may also include other actions (not shown), such as, for example, trimming the hypotube or elongate flexible tube structure; terminating either end of the catheter with various ports, tools or sensors; installing a guidewire structure; testing the overall catheter; etc.

A number of implementations have been described. Nevertheless, it will be understood that various modifications may be made without departing from the spirit and scope of this document. For example, although primarily described in the context of a cryotherapy catheter for treating atrial fibrillation, a two-part flexible protective layer may be employed in any catheter or other medical device having a cross-section whose shape must be maintained as the device is articulated through sharp turns and bends in a patient's body. In particular, catheters with expandable balloons having external vacuum lumens used to aspirate vulnerable plaque from blood vessels may also benefit from a two-part flexible protective lumen, for example, to prevent a vacuum lumen used to perform the aspiration from being constricted. Accordingly, other implementations are within the scope of the following claims.

What is claimed is:

1. A cryotherapy catheter comprising:
   a cryotherapy distal end portion having an inner chamber and an outer surface to contact body tissue to provide cryotherapy; and
   an elongate member having lumens formed therein that provide cryotherapy fluid from a proximal end of the elongate member to the distal end portion inner chamber and channel exhaust proximally from the distal end portion inner chamber, the elongate member comprising an outer generally tubular structure comprising, firstly, an inner tube structure of rigid material having a circumferential cut through at least a portion of a longitudinal length of the inner tube structure to allow bending of the circumferentially-cut portion of the inner tube structure while substantially maintaining a uniform cross-sectional area and shape at a point of bending, and secondly, a separate outer tube that surrounds and is spaced apart from at least the circumferentially-cut portion of the inner tube structure, the separate outer tube being attached in a sealed manner to a proximal end of the cryotherapy distal end portion.

2. The cryotherapy catheter of claim 1, wherein the outer surface comprises an expandable balloon.

3. The cryotherapy catheter of claim 2, wherein the expandable balloon is adapted to contact substantially all of a circumference of an ostium of a patient's pulmonary vein when the expandable balloon is disposed inside the patient's left atrium and inflated substantially outside and adjacent to the pulmonary vein.

4. The cryotherapy catheter of claim 1, wherein the inner chamber comprises a second expandable balloon.

5. The cryotherapy catheter of claim 4, wherein the expandable balloon substantially surrounds the second expandable balloon to define a safety chamber that is in fluid communication with a vacuum lumen extending through the elongate member.

6. The cryotherapy catheter of claim 1, wherein the circumferential cut is a helical cut having a pitch characterized by a distance between two adjacent rotations of the helical cut.

7. The cryotherapy catheter of claim 6, wherein the pitch varies over the portion of the longitudinal length.

8. The cryotherapy catheter of claim 7, wherein the pitch is more fine near a distal end and more coarse near a proximal end of the portion of the longitudinal length.

9. The cryotherapy catheter of claim 1, wherein the circumferential cut is discontinuous.

10. The cryotherapy catheter of claim 1, wherein the circumferential cut extends to a portion of the inner tube structure proximal to the cyrotherapy distal end portion.

11. The cryotherapy catheter of claim 1, further comprising:
    a supply lumen within the elongate member to supply the cryotherapy distal end portion with cryo coolant; and
    an exhaust lumen within the elongate member to exhaust the cryo coolant from the cryotherapy distal portion,
    wherein the inner tube structure prevents the supply and exhaust lumens from being pinched off when the elongate member is bent.

12. A method of manufacturing a cryotherapy catheter, the method comprising providing an elongate member having an outer structure forming an elongate flexible tube structure, introducing within the flexible tube structure a rigid tube structure having a coiled cut therein through at least a portion of a longitudinal length of the rigid tube structure to allow bending of the rigid tube structure without pinching off an inner channel formed by the coiled-cut rigid tube structure, and attaching the flexible tube structure to a cryotherapy distal portion in a sealed manner.

13. The method of claim 12, further comprising extruding the elongate member apart from the rigid tube structure.

14. The method of claim 13, wherein extruding the elongate member comprises extruding the elongate member such that the elongate member has an inner diameter that is approximately 0.002" to 0.004" greater than an outer diameter of the rigid tube structure.

15. The method of claim 12, further comprising introducing within the rigid tube structure at least two lumens to supply the cryotherapy distal portion with cryo coolant and to exhaust the cryo coolant from the cryotherapy distal portion.

16. The method of claim 12, further comprising cutting the rigid tube structure in a coiled manner by rotating the rigid tube and longitudinally advancing the rigid tube relative to a cutting tool.

17. The method of claim 16, wherein cutting the rigid tube structure comprises cutting the rigid tube at a pitch that varies over a length of the portion of the longitudinal length.

18. The method of claim 12, wherein the circumferentially-cut extends to a portion of the rigid tube structure proximal to the cyrotherapy distal end portion.

19. The method of claim 12, wherein the circumferentially-cut portion of the rigid tube structure is radially spaced from any adjacent layer of material.

20. A cryotherapy catheter comprising:
    a cryotherapy distal end portion having an inner chamber and an outer surface to contact body tissue to provide cryotherapy; and
    an elongate member having lumens formed therein that provide cryotherapy fluid from a proximal end of the elongate member to the distal end portion inner chamber and channel exhaust proximally from the distal end portion inner chamber, the elongate member comprising an outer generally tubular structure comprising, firstly, an inner tube structure of rigid material having a circumferential cut through at least a portion of a longitudinal length of the inner tube structure to allow bending of the circumferentially-cut portion of the inner tube structure while substantially maintaining a uniform cross-sectional area and shape at a point of bending, and secondly, a separate outer tube that surrounds and is spaced apart from at least the circumferentially-cut portion of the inner tube structure, the separate outer tube being attached in a sealed manner to a proximal end of the cryotherapy distal end portion, wherein the circumferentially-cut portion of the inner tube structure is radially spaced from any adjacent layer of material.

* * * * *

UNITED STATES PATENT AND TRADEMARK OFFICE
CERTIFICATE OF CORRECTION

| | |
|---|---|
| PATENT NO. | : 7,785,289 B2 |
| APPLICATION NO. | : 11/582156 |
| DATED | : August 31, 2010 |
| INVENTOR(S) | : Jaime Rios and Maritess E. Minas |

Page 1 of 1

It is certified that error appears in the above-identified patent and that said Letters Patent is hereby corrected as shown below:

Column 12, Claim 10, Line 16: delete "cyrotherapy" and insert --cryotherapy--.

Column 12, Claim 18, Line 56: delete "cyrotherapy" and insert --cryotherapy--.

Signed and Sealed this

Seventh Day of December, 2010

David J. Kappos
*Director of the United States Patent and Trademark Office*